United States Patent [19]

Bruzzese

[11] Patent Number: 5,750,572
[45] Date of Patent: May 12, 1998

[54] SALTS OF A POLYUNSATURATED FATTY ACID AND PHARMACEUTICAL FORMULATIONS CONTAINING THEM

[75] Inventor: Tiberio Bruzzese, Milan, Italy

[73] Assignee: Prospa B.V., Hoofdorp, Netherlands

[21] Appl. No.: 649,707

[22] PCT Filed: Nov. 28, 1994

[86] PCT No.: PCT/EP94/03943

§ 371 Date: Jul. 5, 1996

§ 102(e) Date: Jul. 5, 1996

[87] PCT Pub. No.: WO95/16661

PCT Pub. Date: Jun. 22, 1995

[30] Foreign Application Priority Data

Dec. 14, 1993 [IT] Italy ................... MI93A2612

[51] Int. Cl.⁶ ................ A61K 31/20; C07C 229/00; C07C 57/02

[52] U.S. Cl. ............... 514/560; 562/561; 562/562; 562/598

[58] Field of Search ............... 514/560; 562/561, 562/562, 598

[56] References Cited

U.S. PATENT DOCUMENTS

| | | | |
|---|---|---|---|
| 3,952,035 | 4/1976 | Galantay et al. | 260/413 |
| 5,502,077 | 3/1996 | Breivik et al. | 514/560 |

FOREIGN PATENT DOCUMENTS 2216418 10/1989 United Kingdom .

*Primary Examiner*—Raymond Henley, III
*Attorney, Agent, or Firm*—Walter H. Schneider

[57] ABSTRACT

4,7,10,13,16,19-cis-Docosahexaenoic acid (DHA) salts with basic amino acids, in particular arginine and lysine, have favorable therapeutic and technological characteristics compared with the acid.

4 Claims, No Drawings

SALTS OF A POLYUNSATURATED FATTY ACID AND PHARMACEUTICAL FORMULATIONS CONTAINING THEM

This is a 371 of PCT/EP94/03943 filed Nov. 28, 1994.

The present invention relates to the salts of a polyunsaturated fatty acid of the omega-3 series, i.e. 4,7,10,13,16, 19-cis-docosahexaenoic acid (in the following names DHA) with basic amino acids. It should be understood that the invention comprises both the amino acids in the natural laevo form and in the dextro form and also the racemic forms. Preferred amino acids are arginine and lysine.

DHA is obtained from natural sources containing it (fish oils) through chemical-physical methods leading to an acid of high purity (higher than 90%), or alternatively to enriched mixtures, in which it is together with other polyunsaturated fatty acids of the omega-3 series. The mixtures are also used in therapy or as food supplementers, therefore the invention comprises salts of DHA, which is either pure or present as a component of enriched mixtures.

DHA, together with 5,8,11,14,17-cis-eicosapentaenoic acid (in the following names EPA), is the more interesting component of the group of the polyunsaturated omega-3 fatty acids, present in fish oils. Said acids were recently object of a marked interest, since they have shown important therapeutical properties against various diseases of the cardiocirculatory system (thrombosis, aterosclerosis, platelet hyper-aggregation, and the like; see New Engl. J. Med., 318, 549, 1988), diseases of inflammatory origin (see J. Biol. Chem., 359, 7615, 1984), and some tumour forms (see Acta Med. Scand., 220, 69, 1976). The therapeutical efficacy of DHA and of polyunsaturated omega-3 acids, moreover, is also directed to a wide range of other pathological conditions, such as hyperlipemia and hypercholesterolemia, psoriasis, immune and nervous (central and peripheral) disorders, disorders of memory and learning, etc. In the studies carried out up to now, DHA showed a pharmacological profile and biological characteristics similar, but not superimposable, to those of EPA, both in terms of activity range and of potency of action (for example a higher anti-platelet aggregation activity). The administration of DHA increases its in vivo level in tissue phospholipids.

Particularly interesting is that, in principle, DHA is present in phospholipids in a much higher amount than EPA. Since DHA is known to be partly converted into EPA in vivo, it can also be considered as a potential form for the storage of EPA.

In man, DHA is present in a particularly high amount in phospholipids of the brain, retina and testes (from 20 to 40% of fatty acid content); the meaning and the function of this presence is up to now an object of research (v. New Engl. J. Med., 318, 549, 1988). From what is stated above, the importance of DHA both for its own physiological and pharmacological actions and as an EPA source or precursor in vivo is clear.

DHA, with EPA, is widely present in oils of sea origin (fish oils), in which it is present mainly as a triglycerid, together with other acids both unsaturated and saturated, from which it can be obtained both as an enriched mixture and in a very pure form.

From the pharmaceutical technology point of view, DHA and the glycerids or esters thereof are in the form of thick oily liquids, completely insoluble in water, and can accordingly be formulated in practice only in soft gelatin capsules. Therefore, the liquid formulations connected with the presence of water are excluded, from which the oily phase would separate also in the presence of any organic solvents (which on the other hand would be unsuitable for toxicity reasons) used to improve solubility.

Apparently, the easiest method to make DHA water soluble, i.e. salification with alkali metals, proved to be impracticable since the resulting salts give strongly basic aqueous solutions which therefore are poorly tolerated.

An EPA sale with lysine, used to prevent cyclosporin nephrotoxicity, is known from literature (Transplant. Proc., 24, 6, 2583, 1992).

Now it has surprisingly been found that unpredictable, high advantages can be obtained, not only in view of capability to prepare different types of formulations, but also from the biological and pharmacological point of views, using DHA salts with basic amino acids, particularly arginine and lysine. These salts are novel derivatives, never prepared up to now, which are obtained treating aqueous suspensions of DHA, or of DHA-enriched mixtures, with a suitable amount of an amino acid, under stirring at 0°–20° C. In some minutes, clear solutions are obtained which, if necessary, are washed with hexane or ligroin and evaporated to dryness under high vacuum at low temperature, or subjected to freeze-drying. The resulting salts are in the form of very thick, transparent oils, which transform into solids of waxy appearance and consistency at low temperatures. Elementary analysis is consistent with the expected composition, and IR spectrum shows the peaks characteristic of carboxylate ion (—COO) at about 1560 $cm^{-1}$ and 1395 $cm^{-1}$, thus confirming the occurred salification.

Alternatively, the salts are obtained stirring at 0°–20° C. suitable amounts of DHA and of an amino acid, preferably diluting the mixture with an organic solvent, such as ethanol.

In some minutes a clear solution forms, from which the salt is recovered by evaporating the solvent under vacuum.

According to a further method, the novel salts are obtained by double exchange between DHA alkali salts and an amino acid salt, such as the hydrochloride.

These salts are well soluble in water, in which they give solutions of pH not higher than 8, suitable for the preparation of any kind of liquid pharmaceutical formulations, such as injectables, drinkable vials, drops, syrups, lotions for topical use, aqueous creams, etc. Depending on the requirements, together with the active ingredient, the most suitable adjuvants and excipients are used.

Due to the water-solubility characteristics thereof, the salts of the present invention are suitable for the manufacture of granulates, optionally the thromboxane and prostacyclin classes) of an higher insaturation degree, with a reduced platelet-aggregating potential and an higher vasodilating activity. The fact that they are DHA salts with natural amino acids, such as arginine and lysine, warrants that no additional toxicity is present following salification. On the contrary, the presence of two amino acids considered "essential" can be a further advantage when these salts are used as components of liquid formulations for the parenteral nutrition. The well-known detoxyfying action exerted by arginine and lysine adds to the similar DHA action, enhancing it. Of course, the peculiar pharmacological properties of the two amino acids, such as the action stimulating the synthesis of growth hormone by arginine, and the anti-hyperammonia activity of both amino acids are unchanged.

Finally, a further example of favourable interaction between DHA and arginine is evidenced. The latter, in fact, through the guanidine portion of the molecule, is the physiological precursor of the formation—by endothelial cells—of NO, (nitrogen oxide) of which the paramount role in the processes of vascular relaxation and the platelet- aggregation and adhesion activity has recently been acknowledged (see for example Biochem. Biophys. Res. Comm., 153, 3, 1251, 1988). An advantageous complementarity between the DHA vascular activity and that of the arginine used as the salifying agent, and an evident synergistic effect, result.

From the biological-therapeutical point of view, the preferred salt among those claimed in the present invention is the DHA arginine salt.

The anti-platelet aggregation activity of DHA arginine salt was tested in vitro on platelets according to Born's method (Nature, 194, 927, 1962). Platelet enriched plasma was prepared by centrifugation of human venous blood from healthy volunteers. After adding ADP to platelet-enriched plasma, in such an amount as to obtain a 2 micromolar concentration, platelet aggregation was measured in the presence of a 2 micromolar concentration of DHA arginine salt. For comparison, the aggregation induced by ADP in the presence of DHA acid and EPA lysine salt, again in a 2 micromolar concentration, was determined.

Aggregation was expressed as maximal percent decrease of the optical density, at 5 minutes at a 600 µm wavelength. The obtained values are reported in the following:

|                     | Aggregation |
|---------------------|-------------|
| ADP                 | 53.5%       |
| 0ADP + DHA arginine salt | 24.4%   |
| ADP + DHA           | 33.2%       |
| ADP + EPA lysine salt | 40.1%     |

The following examples illustrate the invention, without limiting it.

EXAMPLE 1

32.8 g of 4,7,10,13,16,19-cis-docosahexaenoic acid (DHA, titre 90%) are suspended in 140 ml of distilled water and kept under stirring at room temperature. After that, under cooling, 17.4 g of arginine dissolved in the minimum amount of water are added, keeping stirring for 10 minutes, thus obtaining a complete dissolution. The solution is washed with 50 ml of petroleum ether and evaporated to dryness under reduced pressure and temperature, thus obtaining DHA arginine salt in a nearly theoretical yield.

The elementary analysis of the product (C,H,N,O,) and the acid and base titres are consistent with the expected ones.

IR Spectrum: peak of carboxylate ion at 1560 cm$^{-1}$ and 1395 cm$^{-1}$.

EXAMPLE 2

A solution of 16.4 g of DHA in ethanol is treated with 8.7 g of finely powdered arginine, under stirring at room temperature. After some minutes, the resulting solution is decolourized with carbon and evaporated to dryness at reduced temperature and pressure. The residue is washed with 50 ml of petroleum ether (b.p. 40°–70° C.) and dried again under vacuum, to obtain the DHA arginine salt in an almost theoretical yield.

The chemical-physical and analytical characteristics of the product are consistent with those reported in Example 1.

EXAMPLE 3

32.8 g of DHA (titre 90%) are suspended in 160 ml of distilled water and treated with 14.6 g of lysine, under stirring, then dissolved in a small amount of water. The resulting solution is stirred for 10 minutes, washed with 50 ml of petroleum ether and evaporated to dryness under reduced pressure and temperature, to obtain 46.5 g of DHA lysine salt.

The elementary analysis of the product (C,H,N,O) and the acid and base titres are consistent with what expected.

IR Spectrum: carboxylate ion peak at 1550 cm$^{-1}$ and 1400 cm$^{-1}$.

EXAMPLE 4

32.8 g of DHA dissolved in 120 ml of ethanol are kept under slow stirring and added with 14.6 g of finely powdered lysine, cooling to 0° C. The starting mixture becomes a solution after some minutes. After a further 10 minutes under stirring, the solution is decolourized with active carbon and evaporated to dryness under vacuum. The residue is washed with 50 ml of hexane, and dried again under vacuum, to obtain 46 g of DHA lysine salt.

The chemical-physical and analytical characteristics of the product are consistent with those reported in Example 3.

EXAMPLE 5

32.8 of a mixture of polyunsaturated fatty acids from fish oil, enriched in DHA (DHA=45%), is suspended in 140 ml of distilled water and kept under stirring at room temperature. 16.5 g of arginine dissolved in a small amount of water are added thereto, keeping stirring for 10 minutes, to obtain an opalescent solution. The solution is washed with 50 ml of petroleum ether, which extracts opalescence, and evaporated to dryness under reduced pressure. 47.3 g of a thick oil are obtained, which is soluble in water and contains 31.5% of DHA (determined by means of GC).

EXAMPLE 6

The procedure of Example 5 is followed, starting from 32.8 g of a fatty acid mixture enriched with 45% DHA, and 13.8 g of lysine. 44.5 g of a thick oil are obtained, which is soluble in water and contains 32.9% of DHA (determined by means of GC).

EXAMPLE 7

Formulation in gelatin capsules
DHA arginine salt (459.1 mg), equivalent to DHA mg 300
Triacetin mg 100
Gelatin mg 127
Glycerol mg 62
Sodium ethyl p-hydroxybenzoate mg 0.58
Sodium propyl p-hydroxybenzoate mg 0.29
Vitamin E mg 1

EXAMPLE 8

Formulation in gelatin capsules
DHA arginine salt (mg 153), equivalent to DHA mg 500
Triacetin mg 200
Gelatin mg 325
Glycerol mg 160
Sodium ethyl p-hydroxybenzoate mg 1.5
Sodium propyl p-hydroxybenzoate mg 0.75
Vitamin E mg 2.5.pa

EXAMPLE 9

Formulation in gelatin capsules
DHA lysine salt (mg 722), equivalent to DHA mg 500
Polyethylene glycol 300 mg 200
Gelatin mg 170
Glycerol mg 83
Sodium ethyl p-hydroxybenzoate mg 1
Sodium propyl p-hydroxybenzoate mg 0.5

Vitamin E mg 1
Ascorbyl palmitate mg 2.5

EXAMPLE 10

Formulation in syrup
DHA arginine salt (g 4.59), equivalent to DHA g 3
Saccharose g 50
Methyl p-hydroxybenzoate g 0.075
Ethyl p-hydroxybenzoate g 0.029
Propyl p-hydroxybenzoate g 0.021
Sodium ascorbate g 0.100
Orange flavour g 0.250
Depurated water q.s.to ml 100

EXAMPLE 11

Formulation in syrup
Arginine salt of a mixture enriched in DHA, containing 31.5% of DHA (9.5 g), equivalent to DHA g 3
Saccharose g 50
Methyl p-hydroxybenzoate g 0.075
Ethyl p-hydroxybenzoate g 0.029
Propyl p-hydroxybenzoate g 0.021
Sodium ascorbate g 0.100
Orange flavour g 0.250
Depurated water q.s.to ml 100

EXAMPLE 12

Formulation in drops
DHA lysine salt (43.35 g), equivalent to DHA g 30
Methyl p-hydroxybenzoate g 0.090
Ethyl p-hydroxybenzoate g 0.35
Propyl p-hydroxybenzoate g 0.025
Sodium metabisulfite g 0.300
Orange flavour g 2
Depurated water q.s.to ml 100

EXAMPLE 13

Formulation in lotion
DHA arginine salt (g 15.3), equivalent to DHA g 10
Ethanol g 30
Sodium metabisulfite g 0.3
Perfume Pouce g 0.6
Depurated water q.s.to ml 100

EXAMPLE 14

Formulation in monodose granulate for extemporary oral use
DHA lysine salt (mg 1445) equivalent to DHA mg 1000
Precipitated silica mg 50
Lemon flavour mg 100
Sorbitol q.s.to g 5

EXAMPLE 15

Formulation in tablets for the oral use
DHA lysine salt (mg 361.3) equivalent to DHA mg 250
Precipitated silica mg 50
Microcrystalline cellulose mg 100
Talc mg 10
Magnesium stearate mg 5
Lactose mg 133.5.

What is claimed is:

1. An arginine salt of 4,7,10,13,16,19-cis-docosahexanoic acid (DHA) endowed with anti-platelet aggregating activity in which the acid is greater than 90% pure.

2. A method of preparing an arginine salt of 4,7,10,13,16,19-cis-docosahexanoic acid (DHA) which comprises reacting arginine with DHA of greater than 90% purity, or with a mixture of polyunsaturated acids enriched with DHA of greater than 90% purity, conducting the reaction with stirring in a medium selected from water and lower alcohols at a temperature of 0°–20° C., and recovering the resulting salt from the reaction medium.

3. A pharmaceutical composition endowed with anti-platlet aggregating activity and other activities useful in the therapy of cardiovascular diseases comprising as the principal active ingredient an effective amount of a salt according to claim 1 in admixture with a pharmaceutically acceptable carrier.

4. A method of inhibiting platlet aggregation in a patient which comprises administering to such patient an effective amount of a composition according to claim 3.

* * * * *